(12) United States Patent
Odorzynski (10) Patent No.: US 7,919,666 B2
(45) Date of Patent: Apr. 5, 2011

(54) PERSONAL CARE ARTICLES WITH FRAGRANCE DELIVERY SYSTEM

(75) Inventor: Thomas Walter Odorzynski, Green Bay, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1449 days.

(21) Appl. No.: 10/334,931

(22) Filed: Dec. 31, 2002

(65) Prior Publication Data

US 2004/0127866 A1    Jul. 1, 2004

(51) Int. Cl.
A61F 13/15    (2006.01)
A61F 13/20    (2006.01)

(52) U.S. Cl. ........................ 604/359; 604/367

(58) Field of Classification Search .............. 604/359, 604/385.06, 367, 358
See application file for complete search history.

(56) References Cited

U.S. PATENT DOCUMENTS

| | | | |
|---|---|---|---|
| 2,066,946 A * | 1/1937 | Reiman | 604/359 |
| 2,615,754 A * | 10/1952 | Lindenberg | 239/36 |
| 3,516,846 A | 6/1970 | Matson | |
| 3,516,941 A | 6/1970 | Matson | |
| 3,645,060 A | 2/1972 | Hammond | |
| 3,783,869 A * | 1/1974 | Schnipper | 604/304 |
| 3,849,241 A | 11/1974 | Butin et al. | |
| 3,996,156 A | 12/1976 | Matsukawa et al. | |
| 4,041,203 A | 8/1977 | Brock et al. | |
| 4,087,376 A | 5/1978 | Foris et al. | |
| 4,100,324 A | 7/1978 | Anderson et al. | |
| 4,186,743 A * | 2/1980 | Steiger | 604/359 |
| 4,242,854 A | 1/1981 | Nissen | |
| 4,317,449 A | 3/1982 | Nowakoski | |
| 4,409,156 A | 10/1983 | Hoshi et al. | |
| 4,483,759 A | 11/1984 | Szycher et al. | |
| 4,493,869 A | 1/1985 | Sweeny et al. | |
| 4,654,256 A | 3/1987 | Doree et al. | |
| 4,699,823 A | 10/1987 | Kellenberger et al. | |
| 4,720,415 A | 1/1988 | Vander Wielen et al. | |
| 4,752,496 A | 6/1988 | Fellows et al. | |
| 4,753,646 A | 6/1988 | Enloe | |
| 4,777,073 A | 10/1988 | Sheth | |
| 4,781,962 A | 11/1988 | Zamarripa et al. | |
| 4,790,836 A * | 12/1988 | Brecher | 604/359 |
| 4,808,408 A | 2/1989 | Baker et al. | |

(Continued)

FOREIGN PATENT DOCUMENTS

EP    0509409 A1    10/1992

(Continued)

OTHER PUBLICATIONS

Internet Pages, Aromatherapy Basics, Sep. 19, 2002.

(Continued)

*Primary Examiner* — Michele Kidwell
(74) *Attorney, Agent, or Firm* — Dority & Manning, PA (57) ABSTRACT

Personal care articles are provided having odor control patches thereon. The patches include a cavity that house one or more fragrant materials or odor absorbing materials. A portion of the patch is detachable in order to expose and release the odor control materials contained therein. The patches can be removably-attached to the personal care article thereby allowing the patch to be affixed to the personal care articles at the time of manufacture or by the consumer just prior to use. The personal care articles are provided with an air-permeable pocket to house the patch and cover odor absorbing materials when the cavity is exposed.

51 Claims, 6 Drawing Sheets

U.S. PATENT DOCUMENTS

| | | |
|---|---|---|
| 4,818,600 A | 4/1989 | Braun et al. |
| 4,828,556 A | 5/1989 | Braun et al. |
| 4,861,652 A | 8/1989 | Lippert et al. |
| 4,880,690 A | 11/1989 | Szycher et al. |
| 4,908,252 A | 3/1990 | Carnahan et al. |
| 4,961,493 A | 10/1990 | Kaihatsu |
| 4,965,122 A | 10/1990 | Morman |
| 5,043,161 A | 8/1991 | Scarpelli et al. |
| 5,071,704 A | 12/1991 | Fischel-Ghodsian |
| 5,093,182 A | 3/1992 | Ross |
| 5,122,407 A | 6/1992 | Yeo et al. |
| 5,180,637 A | 1/1993 | Sumii |
| 5,188,236 A | 2/1993 | Sayers et al. |
| 5,284,703 A | 2/1994 | Everhart et al. |
| 5,290,268 A | 3/1994 | Oliver et al. |
| 5,297,732 A | 3/1994 | Hahn |
| 5,361,905 A | 11/1994 | McQueeny et al. |
| 5,364,382 A | 11/1994 | Latimer et al. |
| 5,382,400 A | 1/1995 | Pike et al. |
| 5,385,775 A | 1/1995 | Wright |
| 5,391,420 A | 2/1995 | Bootman et al. |
| 5,392,590 A | 2/1995 | Ambrose et al. |
| 5,415,640 A | 5/1995 | Kirby et al. |
| 5,458,592 A | 10/1995 | Abuto et al. |
| 5,514,470 A | 5/1996 | Haffner et al. |
| 5,527,300 A | 6/1996 | Sauer |
| 5,549,775 A | 8/1996 | Odorzynski |
| 5,599,338 A | 2/1997 | Enloe |
| 5,601,542 A | 2/1997 | Melius et al. |
| 5,607,551 A | 3/1997 | Farrington, Jr. et al. |
| 5,651,778 A | 7/1997 | Melius et al. |
| 5,707,707 A | 1/1998 | Burnes et al. |
| 5,714,107 A | 2/1998 | Levy et al. |
| 5,769,832 A | 6/1998 | Hasse |
| 5,769,833 A | 6/1998 | Hasse |
| 5,858,515 A | 1/1999 | Stokes et al. |
| 5,951,534 A | 9/1999 | Cummings et al. |
| 5,994,615 A | 11/1999 | Dodge, II et al. |
| 6,004,307 A | 12/1999 | Colon et al. |
| 6,013,063 A * | 1/2000 | Roe et al. ............... 604/385.23 |
| 6,075,179 A | 6/2000 | McCormack et al. |
| 6,099,516 A | 8/2000 | Pozniak et al. |
| 6,111,163 A | 8/2000 | McCormack et al. |
| 6,129,720 A | 10/2000 | Blenke et al. |
| 6,147,037 A | 11/2000 | Gardlik et al. |
| 6,229,061 B1 | 5/2001 | Dragoo et al. |
| 6,245,693 B1 * | 6/2001 | Gagliardi et al. ............... 442/76 |
| 6,284,261 B1 * | 9/2001 | Tramontana ............... 424/430 |
| 6,315,864 B2 | 11/2001 | Anderson et al. |
| 6,318,555 B1 | 11/2001 | Kuske et al. |
| 6,336,922 B1 | 1/2002 | VanCompel et al. |
| 6,369,290 B1 | 4/2002 | Glaug et al. |
| 6,383,960 B1 | 5/2002 | Everett et al. |
| 6,387,471 B1 | 5/2002 | Taylor et al. |
| 6,403,186 B1 | 6/2002 | Tararuj et al. |
| 6,410,823 B1 | 6/2002 | Daley et al. |
| 6,429,350 B1 * | 8/2002 | Tanzer et al. ............... 604/368 |
| 2002/0148749 A1 | 10/2002 | Briseboi et al. |
| 2003/0115834 A1 * | 6/2003 | Kelley ............... 53/217 |
| 2004/0000596 A1 * | 1/2004 | Cuthbert ............... 239/34 |
| 2004/0043049 A1 * | 3/2004 | Erdman ............... 424/402 |
| 2004/0082927 A1 * | 4/2004 | Littleton et al. ............... 604/346 |

FOREIGN PATENT DOCUMENTS

| | | |
|---|---|---|
| EP | 0510619 A1 | 10/1992 |
| EP | 1090616 A2 | 4/2001 |
| GB | 2311727 A * | 10/1997 |
| WO | WO 9116871 A1 * | 11/1991 |
| WO | WO 93/09818 | 5/1993 |
| WO | WO 9842286 A1 * | 10/1998 |
| WO | 02/069865 A1 | 9/2002 |
| WO | WO 02/094679 | 11/2002 |

OTHER PUBLICATIONS

Internet Pages, Aromatherapy for Women and Children: Pregnancy and Childbirth, Sep. 25, 1998.

Internet Pages, The Guide to Aromatherapy, Sep. 23, 1998.

* cited by examiner

PERSONAL CARE ARTICLES WITH FRAGRANCE DELIVERY SYSTEM

BACKGROUND OF THE INVENTION

Absorbent personal care articles, such as diapers, adult incontinence garments, sanitary napkins, bed pads, panty liners, incontinent pads, and so forth are well known in the art. These articles are inexpensive, often disposable, and yet capable of absorbing and retaining fluids and other bodily discharges. These absorbent personal care articles typically have an outer cover having a liquid-impermeable fabric, such as a plastic film, to prevent the retained discharge from leaking from the article and soiling items of clothing, bedding, furniture, and the like. However, while the articles may proficiently retain the bodily discharges, the odor associated with the same is often released. In this regard, many diapers today employ "breathable" materials in the sense that air and water vapor will pass through the outer cover. Breathable outer covers have become increasingly popular and more highly commercialized in absorbent personal care products, particularly in connection with disposable diapers. The breathable materials help promote airflow in and around an infant's skin and this exchange of air helps reduce the levels of moisture adjacent the skin. Reducing levels of entrapped moisture in turn, helps prevent diaper rash and other skin conditions. However, while healthy for the infant's skin, increased airflow can likewise increase the release of unpleasant odors from the diaper. Thus, mechanisms for masking and/or absorbing odors emanating from within soiled personal care articles are desirable.

In addition, apart from controlling unpleasant odors, various fragrances or perfumes are commonly employed simply for their pleasing aroma. Further, certain aromas have also been specifically employed in folk remedies as well as what is commonly referred to as "aromatherapy." In this regard, certain aromas are believed to help individuals obtain or reach certain moods or feelings, such as sleepiness, relaxation and so forth. Certain essential oils have commonly been employed in this respect. Thus, mechanisms that allow for the controlled application of one or more such aromas in conjunction with a personal care article are likewise desirable.

SUMMARY OF THE INVENTION

In one aspect of the present invention, a personal care article is provided comprising: first and second encasing layers; an absorbent core positioned between said first and second encasing layers; a patch including an odor control agent; and an outermost porous layer having a Frazier air permeability of at least about 10 m$^3$/m$^2$/minute and wherein said outermost porous layer extends over at least a portion of the first encasing layer and the patch, and further wherein the patch is located between the outermost porous layer and the first encasing layer. In one embodiment, the first encasing layer can comprise a liquid impermeable outer cover and the second encasing layer a liquid permeable liner. In an alternate embodiment, the first encasing layer can comprise a liquid permeable liner and the second encasing layer a liquid impermeable outer cover. The patch desirably includes a sealed cavity, for housing the odor control agent, formed by one or more barrier layers. Further, at least a portion of the barrier layer is removable so as to expose the odor control agent. The odor control agent can, optionally, be contained within or as part of a carrier such as, for example, a polymeric matrix or microcapsules. In one embodiment, the personal care article can also include an adhesive layer positioned between and attaching the patch and outer cover. The patch is desirably positioned adjacent an end margin of the personal care article. Further, the patch can be permanently or releasably-attached to the personal care article. In one embodiment, the porous layer forms a pocket sized to at least substantially house the patch.

In a further aspect, a personal care article is provided comprising a liquid permeable liner; a liquid impermeable outer cover; an absorbent core positioned between the liner and outer cover; and a patch having a sealed containment area with an odor control agent therein. In one embodiment, the patch can include first and second barrier layers wherein at least a portion of the second barrier layer is detachable from the first barrier layer thereby exposing the odor control agent and allowing the same to be discharged from the patch. Further, the first barrier layer can be attached to the outer cover by one or more mechanisms such as, for examples, adhesives, mechanical fasteners, and so forth. In one embodiment, a portion of the second barrier layer, adjacent an edge of the patch, can be unattached to the first barrier layer in order to facilitate removal of the same. In a further embodiment, the personal care article can include a cover material extending over and forming a pocket with the liquid impermeable outer cover and wherein the patch is located within the pocket. The cover material, forming the outer portion of the pocket, desirably has a Frazier air permeability greater than about 10 m$^3$/m$^2$/minute.

In a further aspect, an odor control system is provided comprising a package having a front and a back panel connected to one another by a plurality of side panels and wherein said package contains (i) a stack of personal care articles; and (ii) a release sheet having a first planer surface and a second planar surface, and wherein the first planar surface has a plurality of removably-affixed patches thereon. The patches include an odor control agent therein and a means for attaching the patches to one or more of the personal care articles. The release sheet is desirably positioned adjacent said stack and, in one embodiment, the patches are proximate the stack. The patches can have an adhesive layer contacting the first planar surface of the release sheet. Still further, the first planar surface of the release sheet desirably comprises a low adhesion surface. In one embodiment, the personal care articles include a pocket sized to house the patch, the outer portion of which comprises a material having a Frazier air permeability greater than about 10 m$^3$/m$^2$/minute.

DEFINITIONS

As used herein, the term "comprising" is inclusive or open-ended and does not exclude additional unrecited elements, compositional components, or method steps. Accordingly, the term "comprising" encompasses the more restrictive terms "consisting essentially of" and "consisting of."

As used herein the term "fabric" means a material comprising a network of fibers including, but not limited to, woven or knitted materials, tufted or tufted-like materials, nonwoven webs, and so forth.

As used herein the term "nonwoven" or "nonwoven web" refers to a fabric having a structure of individual fibers or threads which are interlaid, but not in an identifiable manner as in a woven or knitted fabric. Nonwoven fabrics or webs can be formed by numerous processes such as for example, meltblowing processes, spunbonding processes, hydroentangling, bonded carded web processes and so forth.

As used herein, the term "personal care product" refers to diapers, training pants, absorbent underpants, adult incontinence products, feminine hygiene products, bed pads, body wraps, bandages, and so forth.

As used herein the term "odor control agents" refers to odor absorbing and/or odor masking agents.

As used herein the term "carrier" refers to any suitable composition or mechanism capable of maintaining and/or containing the odor control agents and further capable of subsequently releasing the odor control agents.

As used herein "Frazier Permeability" is a measure of the permeability of a fabric or web to air. The Frazier Permeability is performed according to Federal Test Standard 191A, Method 5450 dated Jul. 20, 1978, and is reported as an average of three sample readings. Frazier Permeability measures the airflow rate through a web in cubic meters of air per square meter of web per minute.

DESCRIPTION OF THE INVENTION

Absorbent personal care articles generally include a liquid permeable topsheet, which faces the wearer, and a liquid-impermeable backsheet or outer cover. Disposed between the topsheet and outer cover is an absorbent core. In this regard, the topsheet and outer cover are often joined and/or sealed to encase the absorbent core. Although the following description will be made in the context of a disposable diaper, one skilled in the art will appreciate that the concepts of the present invention would also be suitable for use in connection with other types of personal care articles, and including other articles to be worn about or placed adjacent the body. In addition, although the present invention is described in the context of several specific configurations, it will be appreciated that further combinations or alterations of the specific configurations discussed below may be made by one skilled in the art without departing from the spirit and scope of the present invention.

Figure 1:
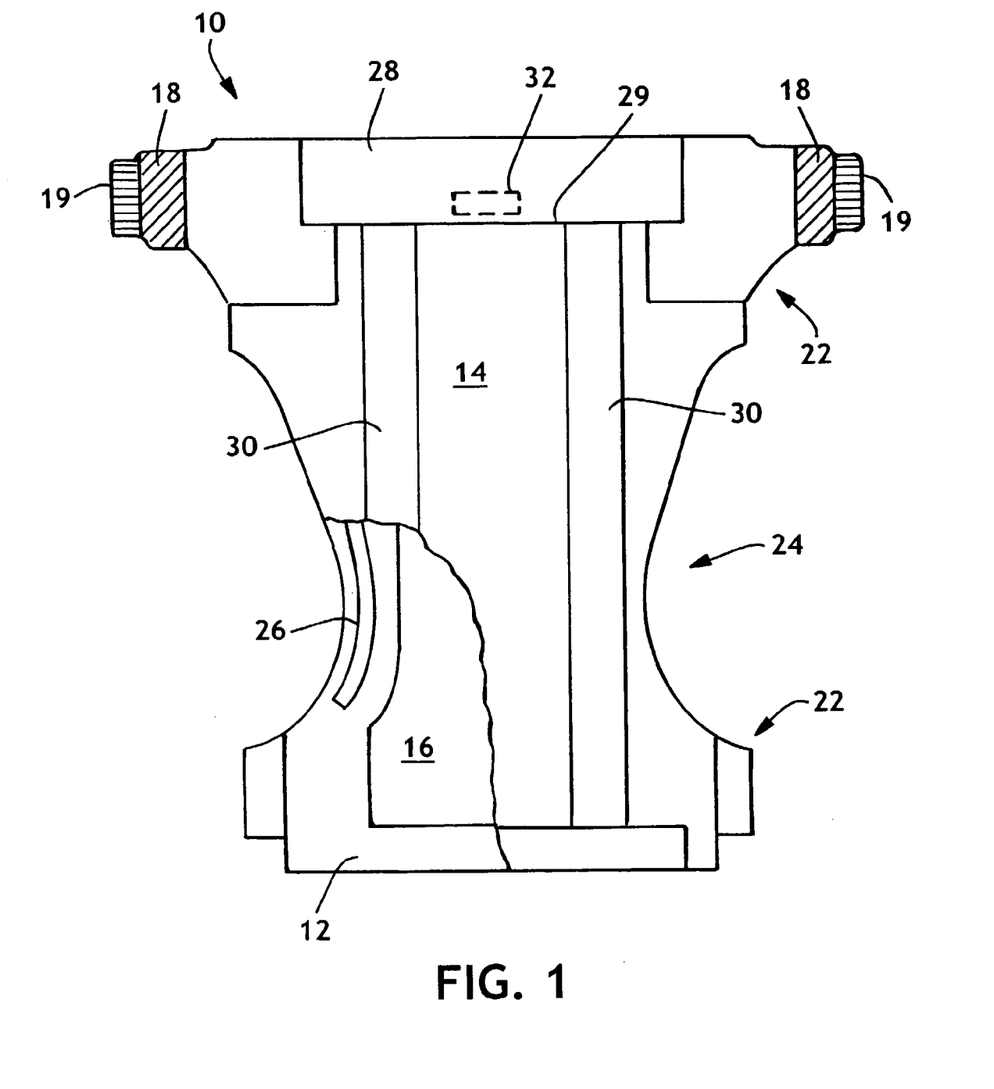
FIG. 1 is a representative partially cut away plan view of a diaper of the present invention in a flat, uncontracted state.

In reference to FIG. 1, a diaper 10 can comprise a liquid-impervious outer cover 12, a liquid permeable topsheet 14 positioned in facing relation to the outer cover 12, and an absorbent core 16 between the outer cover 12 and topsheet 14. The diaper 10 may be of various shapes such as, for example, an overall rectangular shape, T-shape, hourglass shape and so forth. The topsheet 14 is generally coextensive with the outer cover 12 but may optionally cover an area that is larger or smaller than the area of the outer cover 12, as desired. While not shown, it is to be understood that portions of the diaper, such as a marginal section of the outer cover, may extend past and around the terminal edges of the product and form a portion of the body-facing layer. The diaper 10 also has end margins 22 adapted to fit about the waist of the wearer and a central region 24 designed to extend about the groin region as well as provide leg openings in combination with end margins 22. Fastening members 18 are commonly located adjacent the end margins 22 for securing the diaper about the wearer.

The topsheet 14, as representatively illustrated in FIG. 1, desirably presents a body facing surface which is compliant, soft to the touch, and non-irritating to the wearer's skin. The topsheet 14 is desirably employed to help isolate the wearer's skin from liquids held in the absorbent core 16. Topsheets are well known in the art and may be manufactured from a wide variety of materials, such as porous foams, reticulated foams, apertured plastic films, natural fibers (wool, cotton fibers, etc.), synthetic fibers (polyester, polypropylene, polyethylene, etc.), combinations of natural and synthetic fibers, and so forth. Topsheets can comprise a single layer or a multiple layers including a combination of one or more different materials. Nonwoven fabrics, and laminates thereof, are commonly utilized to form topsheets. Suitable topsheet materials include, but not limited to, those described in U.S. Pat. No. 5,382,400 to Pike et al.; U.S. Pat. No. 5,415,640 to Kirby et al.; U.S. Pat. No. 5,527,300 to Sauer; U.S. Pat. No. 5,994,615 to Dodge et al.; U.S. Pat. No. 6,383,960 to Everett et al. and U.S. Pat. No. 6,410,823 to Daley et al.

The backsheet or outer cover 12 comprises a liquid-impervious material. Desirably, the outer cover comprises a material that prevents the passage of water but allows air and water-vapor to pass therethrough. The outer cover can comprise a single layer of material or multiple layers including one or more layers of different materials. In a particular embodiment, the outer cover can comprise a film fixedly attached or bonded to one or more nonwoven webs. The particular structure and composition of the outer cover may be selected from various combinations of films and/or fabrics. In this regard, the outer most layers are generally selected for providing the desired strength, abrasion resistance, tactile properties and/or aesthetics. As an example, nonwoven fabrics are commonly employed as the outermost layer of the outer cover. Suitable outer covers include, but are not limited to, those described in U.S. Pat. No. 4,041,203 to Brock et al.; U.S. Pat. No. 4,777,073 to Sheth; U.S. Pat. No. 4,818,600 to Braun et al.; U.S. Pat. No. 4,828,556 to Braun et al.; U.S. Pat. No. 6,075179 et al. to McCormack et al. and U.S. Pat. No. 6,111,163 to McCormack s et al.

Between the liquid-impervious outer cover 12 and the liquid pervious topsheet 14 is positioned an absorbent core 16. In this regard, the absorbent core often includes one or more absorbent materials including, but not limited to, superabsorbent particles, wood pulp fibers, synthetic wood pulp fibers, synthetic fibers and combinations thereof. A common problem with wood pulp fluff, however, is its lack of integrity and a tendency to collapse when wet. Thus, it is often advantageous to add stiffer reinforcing materials or fibers such as meltblown fibers, staple fibers and so forth. Further, the absorbent materials can be held within a containing fabric or within in a stabilized matrix. The absorbent core may have any of a number of shapes and the size of the absorbent core and selection of materials therein will vary with the desired loading capacity, the intended use of the absorbent article and other factors known to those skilled in the art. Suitable absorbent structures include, but are not limited to, those described in U.S. Pat. No. 4,699,823 to Kellenberger et al.; U.S. Pat. No. 5,364,382 to Latimer et al.; U.S. Pat. No. 5,458,592 to Abuto et al; U.S. Pat. No. 5,601,542 to Melius et al.; U.S. Pat. No. 6,129,720 to Blenke et al.; and U.S. Pat. No. 6,383,960 to Everett et al.

The personal care articles can, optionally, contain one or more additional elements or components. In this regard, numerous additional features and various constructions are known in the art. As but a few examples and in reference to FIGS. 1 and 3, the diaper can further include elastic leg cuffs 26, an elastic waistband 28, fluid control flaps 30 and so forth. By way of example only, additional details regarding the manufacture and/or construction of various personal care articles are described in U.S. Pat. No. 4,753,646 to Enloe; U.S. Pat. No. 4,861,652 to Lippert et al.; U.S. Pat. No. 5,549,775 to Odozynski; U.S. Pat. No. 5,599,338 to Enloe; U.S. Pat. No. 5,651,778 to Melius et al.; U.S. Pat. No. 5,858,515 to Stokes et al.; U.S. Pat. No. 6,099,516 to Pozniak et al.; U.S. Pat. No. 6,336,922 to VanGompel and so forth.

The personal care article of the present invention has a container or patch retaining the odor control agents and optional carrier. The patch is desirably located upon or proximate the exterior portion of the article. In one aspect, the patch is located within the article and/or configured to prevent direct physical contact between the skin and odor control agents. In this regard, many volatile materials can cause skin irritation. Thus, the patch can be positioned within a pocket formed upon the article, under a swatch of material fastened to the article, and so forth. However, in order to obtain sufficient release and diffusion of the odor control agents, the material(s) covering the odor control agents desirably have a porous structure and good air permeability. Thus, the cover materials desirably have a Frazier air permeability greater than about 10 $m^3/m^2$/minute and still more desirably greater than about 30 $m^3/m^2$/minute and still more desirably greater than about 60 $m^3/m^2$/minute. As a specific example, the cover material can have Frazier air permeability between about 30 and 300 $m^3/m^2$/minute or, as a further example, can have a Frazier air permeability of between about 50 and about 250 $m^3/m^2$/minute. The openness or air permeability of the covering material may also be selected in certain instances to control or limit the diffusion of certain highly volatile and/or strong odor control agents. Suitable cover materials include, but are not limited to, nonwoven webs, knitted and/or woven fabrics, porous foams and films, reticulated foams and films, and so forth. Exemplary nonwoven webs include, but are not limited to, spunbond fabrics, bonded carded webs, and laminates thereof. Methods of making the aforesaid cover materials are well known in the art. However, by way of example only, exemplary materials are described in U.S. Pat. No. 3,727,615 to Duchane; U.S. Pat. No. 3,802,817 to Matsuki et al.; U.S. Pat. No. 3,849,241 to Butin et al.; U.S. Pat. No. 4,041,203 to Brock et al.; U.S. Pat. No. 4,100,324 to Anderson et al.; U.S. Pat. No. 4,720,415 to VanderWielen; U.S. Pat. No. 4,781,962 to Zamarripa et al.; U.S. Pat. No. 4,965,122 to Morman; U.S. Pat. No. 5,284,703 to Everhart et al.; U.S. Pat. No. 5,382,400 to Pike et al.; U.S. Pat. No. 5,385,775 to Wright; U.S. Pat. No. 5,707,707 to Burnes et al.; U.S. Pat. No. 5,714,107 to Levy et al.; U.S. Pat. No. 5,858,515 to Stokes et al.; U.S. Pat. No. 6,315,864 to Anderson et al. and so forth.

In a specific embodiment, and in reference to FIG. 1, a waistband 28 or length of other fabric can extend across a portion of an end margin 22 adjacent the upper terminal edge of the diaper 10. The waistband 28 is attached to the article along the side portions and, optionally, adjacent the upper terminal edge of the diaper 10. Thus, the lower edge 29 of the waistband 28 remains unattached to the diaper 10. The patch 32 (shown in phantom) is positioned between the waistband 28 and top sheet 14. The patch 32 can be permanently affixed to the diaper 10 or, in the alternative, can be releasably-attached to the diaper 10. The patch can be attached to the article by means of adhesives, hook and loop fasteners, and other attachment mechanisms known in the art. The patch 32 can be attached to the top sheet 14 during construction of the diaper 10 prior to overlaying and attaching the waistband 28. Alternatively, this particular construction also allows the lower edge 29 of the waistband 28 to be lifted up, away from the topsheet 14, thereby allowing placement of the patch 32 between the topsheet 14 and waistband 28. Thus, it is possible for the patch 32 to be inserted within the diaper 10 at the time of manufacturing or by the consumer just prior to use.

Figure 2:
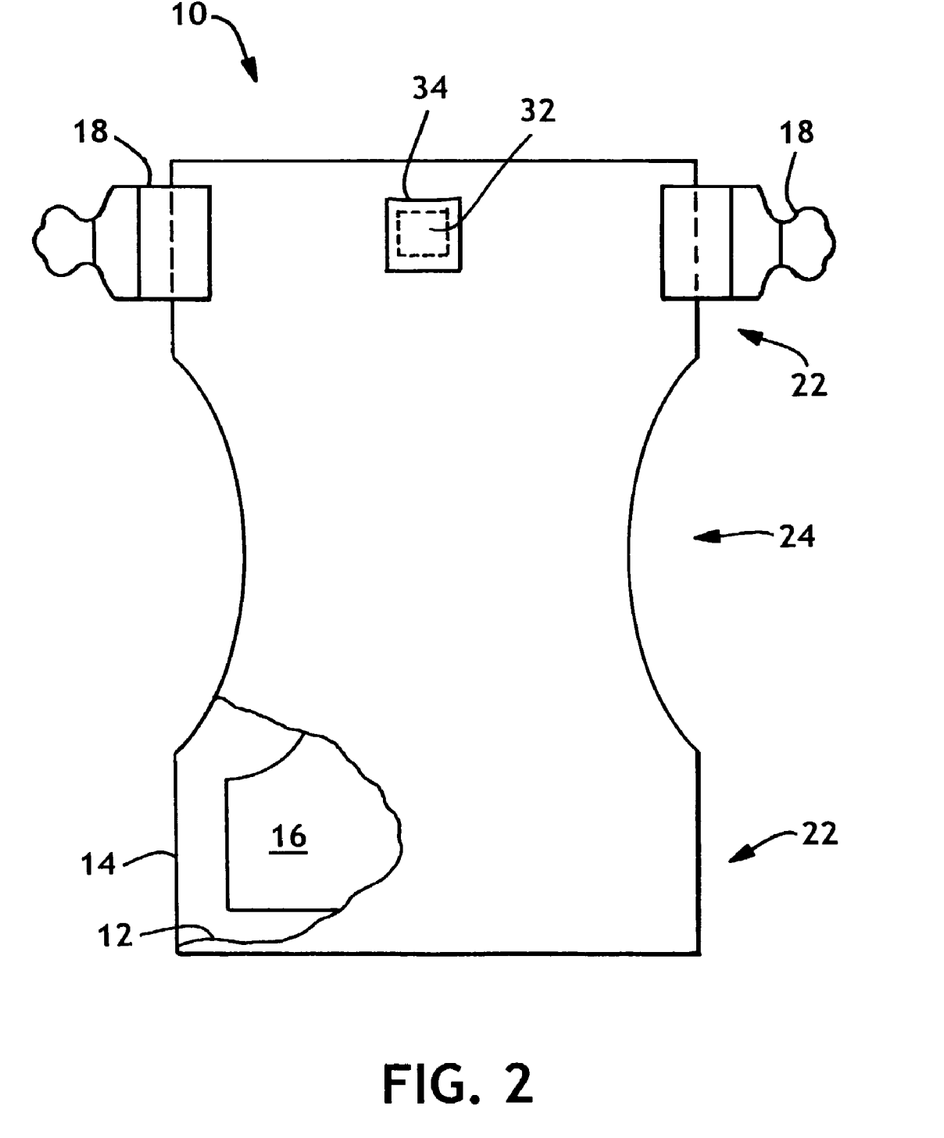
FIG. 2 is a representative partially cut away plan view of a diaper of the present invention in a flat, uncontracted state.

In a further embodiment, and in reference to FIG. 2, a diaper 10 has a pocket 34 formed upon the outer cover 12 for housing the patch 32 (shown in phantom). The pocket 34 is desirably positioned upon or proximate one of the end margins 22 such that the pocket 34 and patch 32 will be positioned adjacent the wearers waist as opposed to the groin region. The pocket can be formed by any of the one or more porous materials described herein-above. In one embodiment, the pocket can be formed by a nonwoven fabric. The pocket can be formed upon or within the outer cover 12 as desired. By way of example only, the pocket 34 can comprise a swatch of fabric attached to the outer cover 12 on three sides such as by mechanical attachment (stitching, crimp bonding, etc.), adhesive bonding, thermal bonding, ultrasonic bonding and so forth.

Figure 3:
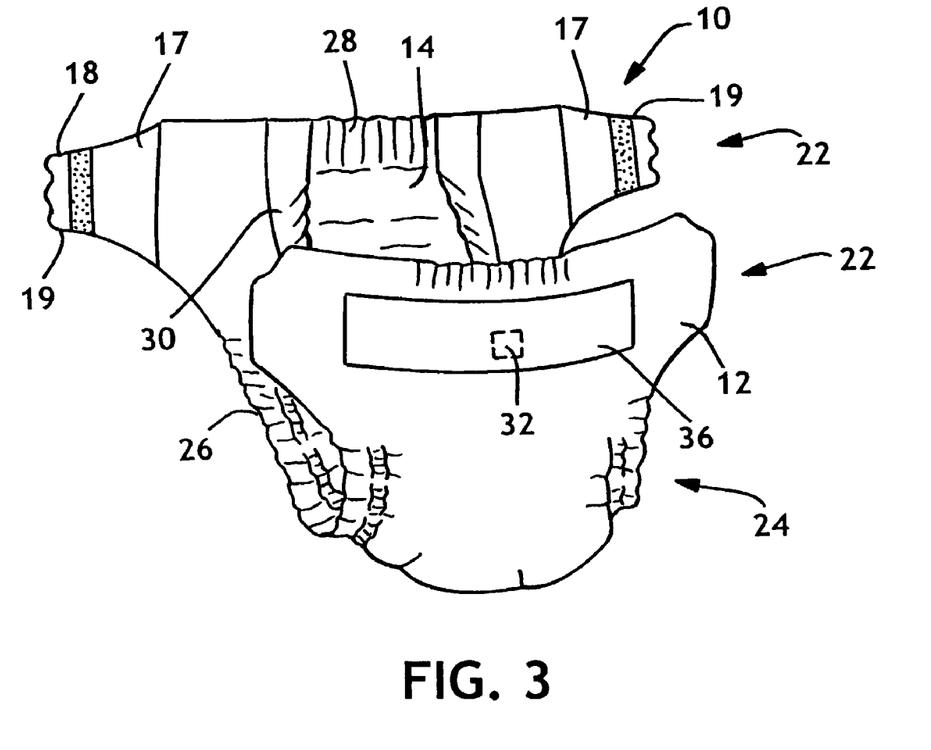
FIG. 3 is a representative partially elevated view of a diaper in a partially contracted state.

In a further embodiment, and in reference to FIG. 3, the diaper 10 employs fasteners 18 such as a "hook and loop" system for fastening the diaper 10 about the wearer (not shown). In a particular embodiment, the fasteners 18 may include a micro-hook material 19 for engaging a loop material 36. Conventional hook and loop fastening systems are, for example, distributed under the designation CS200 by the 3M Company of St. Paul, Minn., USA. Another exemplary micro-hook material is distributed under the designation VELCRO CFM-291058, and is available from VELCRO U.S.A., Inc. of Manchester, N.H., USA. The loop material 36 is desirably positioned upon the outer cover 12 within an end margin 22 of the diaper. The hook and loop attachment system can be configured to close in the front or rear of the diaper as desired. In a specific embodiment, the loop material 36 can be positioned centrally across a portion of an end margin 22. The hook materials 19 are positioned upon the ears or tabs 17 of the diaper such that the tabs 17 can be wrapped around the diaper 10 and releasably-engaged with the loop material 36. Further, the ears or tabs 17 desirably comprise an elastic material in order to improve the fit of the article about the wearer. Exemplary elastic materials include, but are not limited to, those described in U.S. Pat. No. 4,720,415 to Vander Wielen et al.; U.S. Pat. No. 5,385,775 to Wright et al.; U.S. Pat. No. 5,514,470 to Haffner et al.; and U.S. Pat. No. 6,387,471 to Taylor et al.

The loop material 36 can be fixed upon the outer cover using one or more means known in the art and including, but not limited to, mechanical attachment, adhesive bonding, thermal bonding, ultrasonic bonding, and so forth. Desirably, at least a section of the outer edge of the loop material 36 and an adjacent portion thereof remains unaffixed to the outer cover 12. The portion of the loop material 36 remaining unattached to the outer cover is desirably of a size and shape to allow the patch 34 to be inserted between the outer cover 12 and loop material 36 and further inserted such that the patch 36 is at least substantially covered, and even more desirably entirely covered. In this regard, the unaffixed section of the loop material 36 is at least as large as the smallest dimension of the patch, in terms of its length and width. In one embodiment, the unaffixed section is at least as large as the longest dimension of the patch and, optionally, the unaffixed section of the loop material can run the entire length of a side edge. In a further embodiment, the unaffixed section is only slightly larger than either the length or width of the patch. Further, the unaffixed section can be located on any of the four sides of the loop material 36. As indicated above, the patch 32 can be permanently or releasably attached to the outer cover 12. Further, the patch 32 can likewise be included within the diaper 10 during its manufacture or, in the alternative, be provided with the diaper 10 such that the consumer can affix the patch 32 between the outer cover 12 and loop material 36 when, and if, desired. In addition, it will also be understood that more than one patch can be added to the diaper. As specific examples, two, three or four patches can be added to the article as desired.

An exemplary patch desirably comprises a sealed pouch or cavity, formed from one or more barrier layers. In reference to FIG. 4, a patch 50 includes top and bottom barrier layers 52 and 54 respectively, sealed together to form an internal cavity 55 for retaining the odor control agents 56. Each barrier layer 52, 54 is desirably constructed of materials that are impermeable to out-flowing of carriers, odor control agents and any associated vapors and liquids. At least one of the sealed barrier layers 52 is substantially detachable, or otherwise removable from the opposed layer, so as to expose the odor control agents 56 located in the cavity 55 of the patch 50. Removal of the top barrier layer 52, such as by peeling the layer off the patch 50, exposes the internal cavity 55 and results in a release of the odor control agents 56 therefrom. The patch 50 can be manufactured to be readily attachable to other surfaces by including an adhesive material 60 to the bottom barrier layer 54. However, other attachment mechanisms can also be used in conjunction with the bottom barrier layer 54 to fix the patch to the personal care article such as, for example, hook and loop fastening systems and so forth. In addition, the top barrier layer 52 also may include paper or other materials in its upper structure so that labels, instructions, artwork and the like can be applied to the surface thereof. In an alternate embodiment, the patch can comprise a single or continuous layer of barrier material folded over onto itself and sealed about the edges to form a cavity.

Figure 4:
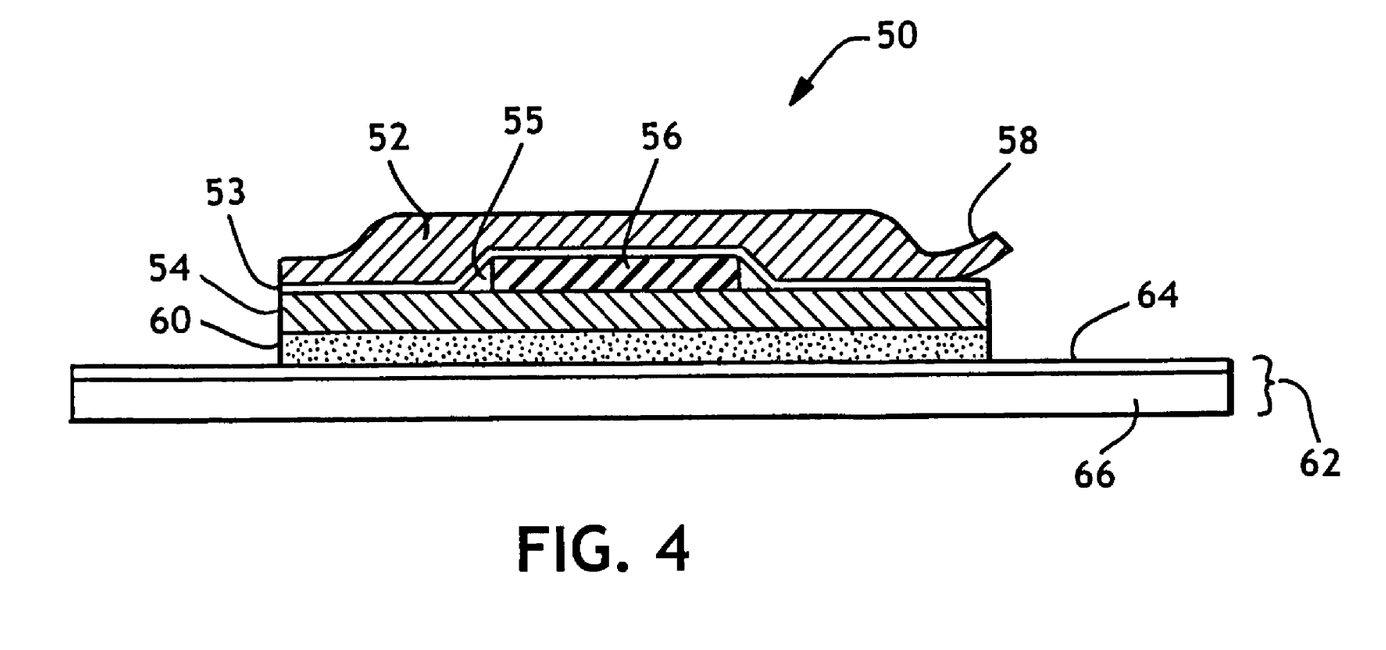
FIG. 4 is a cross-sectional side view of an exemplary patch for maintaining and delivering odor control agents.
Figure 5:
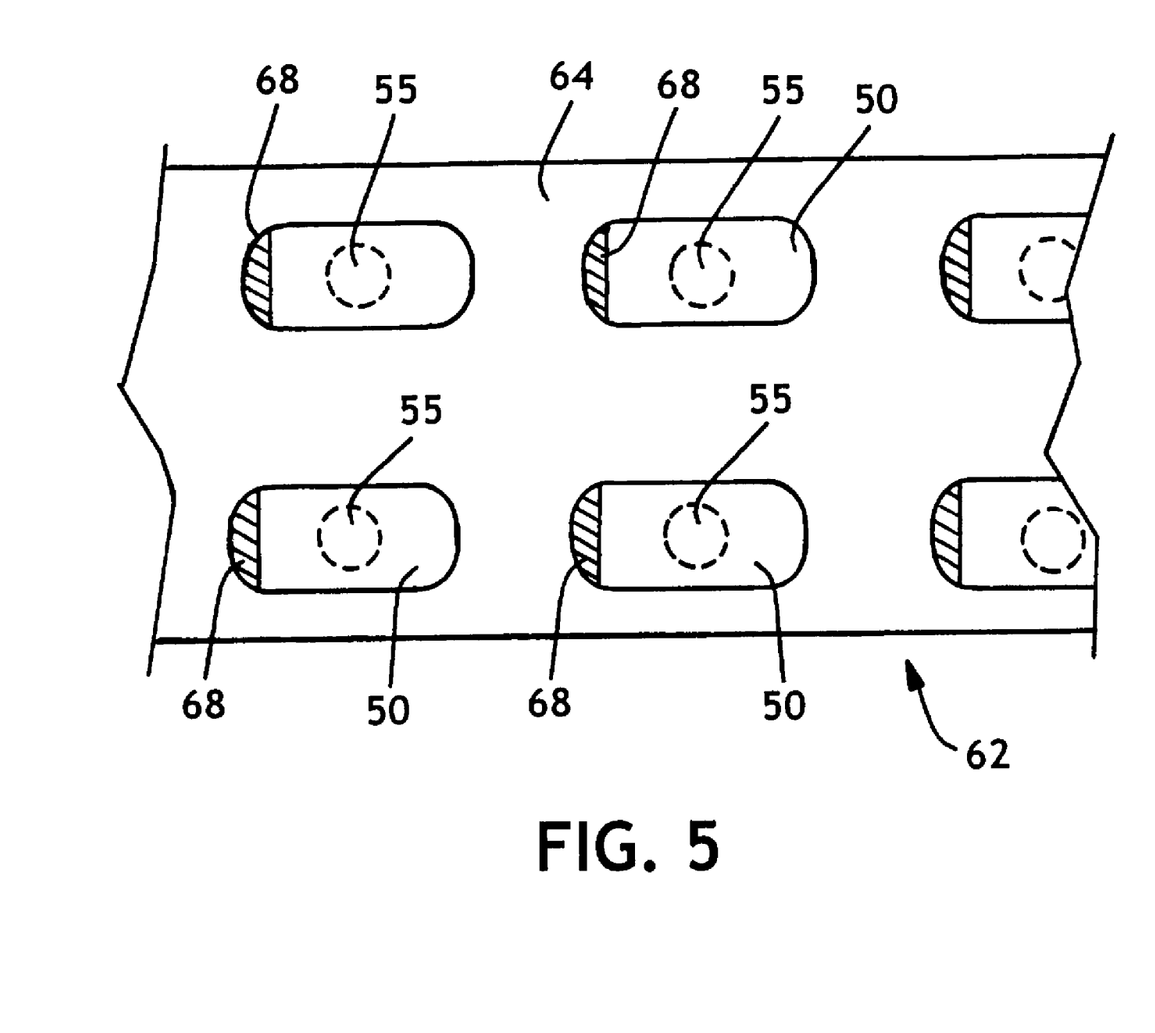
FIG. 5 is a top plan view of a section of a release sheet containing removable patches containing odor control agents.

In reference to FIGS. 4 and 5, the barrier layers 52, 54 can be heat-sealed together around the periphery of the patch 50 in order to hermetically seal the odor control agent 56 within the cavity 55. Desirably, a heat-sealing die uses heat and pressure to fuse the top and bottom barrier layers 52, 54 via an adhesion layer 53 applied to the top barrier layer 52. By way of example only, the adhesion layer 53 can comprise a low melt temperature polymer such as ethylene vinyl acetate (EVA). In order to aid removal of the top barrier layer 52 from the bottom barrier layer 54, a peripheral portion of the patch 50 can remain unsealed such as, for example, an unsealed corner or edge 58. In an alternative embodiment, a pressure sensitive adhesive or other adhesive can be used to form the adhesion layer 53 and seal the top and bottom barrier layers 52 and 54, thereby eliminating the necessity of heat sealing.

The barrier layers 52, 54 of the patch 50 desirably comprise a thin mono-layer or multi-layer material suitable for preventing migration or seepage of odor control agents, for preventing oxygen from moving inside the pouch, and for hermetically sealing to itself or another layer or material. By way of example only, one suitable barrier material is a polyethylene/nylon/polyethylene laminate. The polyethylene and nylon laminate substantially reduces or eliminates seepage of the odor control agents from the cavity as well as the diffusion of oxygen to the inside of the pouch. In this regard, oxygen can degrade the integrity of the adhesive and odor control agent, respectively. As further examples, the barrier layer or layers can comprise a polyvinylidene dichloride (PVDC) type material, nylon, polyethylene, resin coated papers and laminates thereof. An exemplary PVDC material suitable for use within the barrier layer is commercially available under the trade name SARAN from the Dow Chemical Company. Desirably, at least one of the barrier layers is coated with an adhesive material in order to provide a seal between the layers as well as provide for a top layer that is readily removable from the lower layer. An exemplary embodiment of the top barrier member is a laminate comprising paper, polyethylene, metal foil and polyethylene, coated with EVA. Additional details regarding the construction of exemplary patches and methods of making the same are described in U.S. Pat. Nos. 5,391,420 and 4,880,690, the entire contents of each of which are incorporated herein by reference. In addition, one or more rate limiting membranes can be positioned over the cavity and/or between the barrier layers in order to control the rate at which the odor control agents are released from the patch. By way of example only, an exemplary rate limiting membrane is disclosed in U.S. Pat. No. 5,071,704.

When it is intended to allow placement of the patch upon the personal care article by the consumer, it will often be desirable to provide a plurality of patches 50 on larger sheets of a release sheet 62 such as depicted in FIG. 5. In reference again to FIG. 4, the adhesive 60 is located between the outer surface of the bottom barrier layer 54 and the low adhesion surface 64 of support material 66. By way of example only, suitable release sheets can comprise a low-adhesion material such as silicone-coated release paper or silicone-coated MYLAR sheet. The low adhesion surface 64 on the release sheet 62 acts as a release liner, allowing removal of the adhesive 60 from the release sheet 62, thereby resulting in the maintenance of the integrity of the adhesive material 60 on the bottom barrier layer 54 when the patch 50 is removed from the release sheet 62 and applied to the surface of the personal care article as desired. It is also noted that this product configuration readily permits high-speed application from rolls to articles during or after the manufacture of the personal care article. Due to the nature of the release liner, the patches can be readily transferred from the release sheet onto an outer layer of the personal care article by drawing the release sheet over a support roller that turns the flexible release sheet to move at a substantial angle to its original direction. Suction may also be employed to aid in transfer of the patches to the outer surface of the personal care article.

In some embodiments, a carrier can be utilized in conjunction with the odor control agent in order to stabilize the same and help prevent premature or unwanted leakage from the cavity. The carrier can comprise one or more materials adapted to hold the odor control agents and then release the same upon exposure to air. In this regard, numerous carriers for holding and subsequently releasing the odor control agent are believed suitable for use in the present invention. As an example, the odor control agent can be maintained within a polymeric matrix such as a foam or foam-like material. Exemplary foams include, but are not limited to, urethane foams, styrene foams, polyolefin foams, polyvinylchloride foams, silicone foams and so forth. As a further example, the polymeric matrix can in effect be polymerized about or with the odor control agent in order to form a solid polymeric matrix doped with the odor control agent.

In one embodiment, a polymeric precursor can be mixed with the odor control agent and then cured to form a solid polymeric material about the odor control agent. In one embodiment, the top surface of the bottom barrier layer 54 can be coated to a thickness of between about 0.005 cm and about 0.5 cm with a polymeric precursor doped with the odor control agent using an applicator such as a gravure roll, screen coater, and so forth. The odor control agent may simply be dispersed in the polymeric precursor by mechanical application such as, for example, stirring. After application to the bottom barrier layer, the doped polymeric precursor is cured into solid polymeric sections. Curing methods and times will vary with the selected polymer pre-cursors and/or initiators. By way of non-limiting example, exemplary polymers to which odor control agents can be added include the ultraviolet light curable polyurethanes disclosed in U.S. Pat. Nos. 4,880,690 and 4,483,759; the entire contents of the aforesaid references are incorporated herein by reference. As a specific example, doped polymeric matrixes can be formed from a composition including about 10 to 50 weight percent fragrance oil, about 50 to 90 weight percent polyurethane oligomer, and about 1 to 10 weight percent photo-initiator. The amounts may be varied as desired to maximize the aroma and cure speed flexibility of the doped polymer, the flexibility of the pouch and so forth.

In a further embodiment, the carrier can comprise one or more modified cellulosics such as ethyl cellulose, hydroxypropyl cellulose, hydroxyethyl cellulose, methyl cellulose, carboxymethyl cellulose and so forth. As a specific example, a polymer gel mixture suitable for use in the present invention can comprise about 10 to 40 percent by weight fragrance oil, about 30 to 70 percent by weight alcohol (e.g. ethyl alcohol), about 0.1 to 10 percent by weight modified cellulosic, 0 to about 0.1 percent by weight antioxidant, and the balance water.

In still further embodiments, various types of microcapsules and microsponges are suitable for maintaining and releasing the odor control agents. In one aspect, microcapsules encapsulate the odor control agent and upon shearing or rupturing the microcapsule, one or more openings are created in the surface of the microcapsule through which the odor control agent will escape. Generally speaking, one or more substrate sheets are provided and have microencapsulated odor control agent disposed within a binder layer there between. The binder bonds the microcapsules to the substrate sheet and binds together the interior faces of the opposed substrate sheets. Thus, when a user separates the sheets apart, some or all of the microcapsules rupture, thereby exposing and/or releasing the odor control agent contained therein. Microsponges can also be used in connection with the present invention. Microsponges differ from microcapsules in that microsponges are substantially filled with a fragrance or other material as opposed to enveloping the material. However, since microsponges do not fully encapsulate the associated material, merely exposing the microsponge to the air allows the fragrance to diffuse from or otherwise be released from the microsponge. Exemplary microspheres, microsponges and methods of using the same include, but are not limited to, those described in U.S. Pat. Nos. 3,516,941; 3,996,156; 4,409,156; 4,087,376; 4,493,869; 4,654,256; 4,808,408; 4,908,252; 5,043,161 and 5,180,637; each of the aforesaid references are incorporated herein by reference.

When utilizing microcapsules embedded within a binder material, the barrier layers 52, 54 of the patch 50 can comprise a wider range of materials including, but not limited to, polyolefin films, metal foils, metalized films or fabrics, nonwoven fabrics, cellulosic materials, and so froth. In addition, the top barrier layer 52 can optionally include printing that matches or compliments the colors and/or designs upon the personal care article. As a further option, the top barrier layer 52 can include one or more insignias, brand names, etc. In addition, the binder material and odor control agent can likewise be colored or patterned as desired to match or compliment artwork or design upon the personal care article. In still a further embodiment, the microcapsules can be retained by a substantially transparent binder and/or bottom barrier layer 54. While various carrier materials are described herein, it is noted that still other matrixes, gels and sponge-like materials can be used as a carrier in combination with the patch 50.

The odor control agents can comprise any of a variety of materials including viscous and non-viscous liquids such as solutions, emulsions, dispersions, gels and so forth. Further, the odor control agents can also include solids having a distinct smell and that readily volatilize upon exposure to air such as, for example, certain organic solids. In one aspect of present invention, the odor control agents can comprise one or more fragrant materials or materials that provide chemically active vapors. The odor control agents selected should be chosen to be compatible with the barrier materials, binders, and/or any components that they may contact. In one embodiment, the odor control agents can comprise and/or include volatile, fragrant compounds including, but not limited to, perfumes, essences, fragrance oils, and so forth. As is known in the art, many essential oils and other natural plant derivatives contain large percentages of highly volatile scents. In this regard, numerous essential oils, essences, and scented concentrates are commonly available from companies in the fragrance and food businesses. Exemplary oils and extracts include, but are not limited to, those derived from the following plants: almond, amyris, anise, armoise, bergamot, cabreuva, calendula, canaga, cedar, chamomile, coconut, eucalyptus, fennel, jasmine, juniper, lavender, lemon, orange, palm, peppermint, quassia, rosemary, thyme, and so forth.

In a further aspect, the odor control agents can comprise and/or include odor-absorbing materials. Exemplary materials include, but are not limited to, cyclodextrins, zeolites, activated carbon and water-soluble antibacterial compounds, such as cetyl pyridinium chloride, zinc chloride, copper salts, copper ions, chlorhexidine, quaternary ammonium compounds, chelating agents, parabens, chitin, and so forth. Numerous varieties of intermediate zeolites suitable for use herein are commercially available under the trade names ADVERA and VALFOR from PQ Corporation of Valley Forge, Pa., USA.

It is noted that a great number of suitable odor control agents are available and capable of use in the present invention. The selection of the particular agent or agents will vary in accord with the specific personal care article, the desired result (odor masking, odor absorbing, aromatherapy, etc.), user preferences, cost and so forth. Thus, the invention is not intended to be limited by the specific selection of the odor control agents contained therein.

Figure 6:
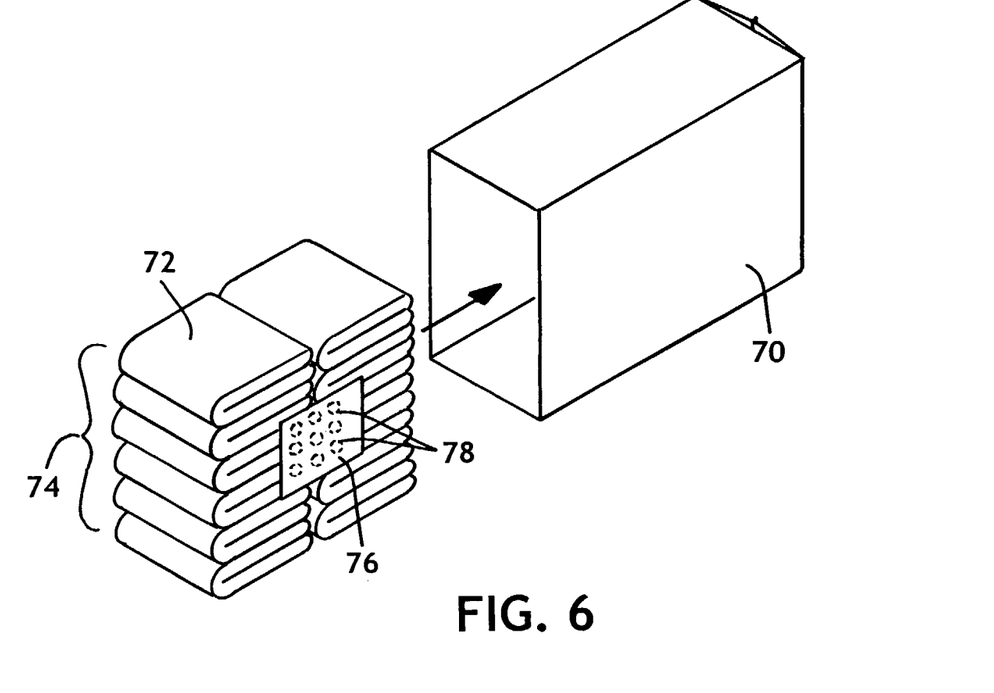
FIG. 6 is a representative view of a stack of diapers and an accompanying release sheet with removable patches configured for loading into accompanying packaging.
Figure 7:
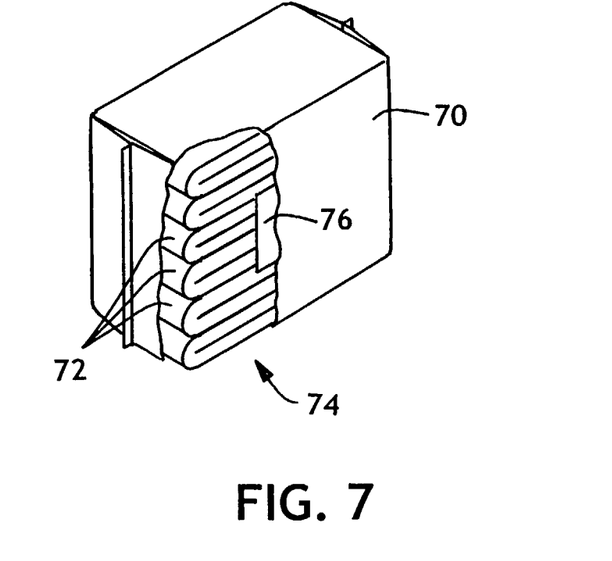
FIG. 7 is a partially elevated, cut-away view of packaging of the present invention.

A system for providing personal care articles having associated attachable odor control patches is also provided. Personal care articles are often compressed and packaged either alone or together with additional articles. Exemplary packaging equipment and/or materials are described in U.S. Pat. No. 3,645,060 to Hammond; U.S. Pat. No. 4,242,854 to Nissen et al.; U.S. Pat. No. 5,361,905 to McQueeny; U.S. Pat. No. 6,318,555 to Kuske et al. and so forth. The personal care articles are commonly compressed together in a stack, the compressed stack is then placed within packaging material, and the packaging material sealed. Suitable packaging material includes, but is not limited to, paper, plastic films, woven fabrics, nonwoven webs, laminate materials and so forth. In reference to FIGS. 6 and 7, packaging 70 includes a plurality of diapers 72 arranged in stacks 74 and a release sheet 76 containing a plurality of patches 78 (shown in phantom). Desirably, the sheet material 76 is provided with the patches 78 contacting the stacks 74 of personal care articles 72 thereby leaving flat sheet material exposed and in contact with the packaging 70 when inserted and sealed therein. By providing the sheet material 74 with the patches 76 facing the personal care articles the potential for ripping the packaging material 70, either during loading or in shipping, is reduced. The sheet material 76 can be superposed with any face of the stack(s) 74 and/or personal care articles 72. By way of example only, and in reference to FIG. 7, packaging 70 is provided comprising multiple stacks 74 of folded, compressed diapers 72. A release sheet 76 is superposed with the stacks 74, spanning the stacks 74, wherein the patches 78 contact the diapers 72 and the backside of the release sheet 76 contacts the packaging 70. The number of patches provided can be more than, less then or equal to the number of personal care articles provided within the packaging and can vary as desired. By way of example only, the ratio of patches to personal care articles can vary between about 10:1 and about 1:10. As a further example, the ratio of patches to personal care articles can vary between about 6:1 and about 1:6. In a specific embodiment, the ratio of patches to personal care articles can be about 1:1. In a further aspect, the release sheet can contain patches having different odor control agents; including, but not limited to, (i) having patches containing different fragrances, (ii) having patches containing different odor absorbing agents, (iii) having patches containing fragrances and patches containing odor absorbing agents, and other combinations as may be desired.

While various patents and other reference materials have been incorporated herein by reference, to the extent there is any inconsistency between incorporated material and that of the written specification, the written specification shall control. In addition, while the invention has been described in detail with respect to specific embodiments and/or examples thereof, it will be apparent to those skilled in the art that various alterations, modifications and other changes may be made to the invention without departing from the spirit and scope of the present invention. It is therefore intended that the claims cover or encompass all such modifications, alterations and/or changes.

What is claimed is:

1. A personal care article comprising:
   first and second encasing layers, wherein said first encasing layer comprises a liquid permeable liner;
   an absorbent core positioned between said first and second encasing layers;
   a patch including an odor control agent, wherein said patch is attached to said first encasing layer; and
   an outermost porous layer directly attached to said first encasing layer, said outermost porous layer having a Frazier air permeability of at least 10 m$^3$/m$^2$/minute and wherein said outermost porous layer extends over at least a portion of said first encasing layer and said patch and further wherein said patch is located between said outermost porous layer and said first encasing layer.

2. The personal care article of claim 1 wherein said second encasing layer comprises a liquid impermeable outer cover.

3. The personal care article of claim 1 wherein said patch includes a sealed cavity formed by at least one barrier layer and wherein said odor control agent is contained within said cavity.

4. The personal care article of claim 1 wherein said patch comprises a first barrier layer and a second barrier layer and wherein said second barrier layer is proximate said outermost porous material and further wherein at least a portion of said second barrier layer is removable.

5. The personal care article of claim 4 wherein said patch contains a carrier and said odor control agent is located within said carrier.

6. The personal care article of claim 4 further comprising an adhesive layer, said adhesive layer positioned between and attaching said first barrier layer of said patch and said first encasing layer.

7. The personal care article of claim 1 wherein said porous layer and said patch are positioned adjacent an end margin of said personal care article.

8. The personal care article of claim 7 wherein said porous layer comprises an elastic band material extending across substantially the entire length of said end margin.

9. The personal care article of claim 1 wherein said odor control agent is maintained within a polymer matrix.

10. The personal care article of claim 5 wherein said carrier comprises microcapsules and further wherein said second barrier layer of said patch is attached to said microcapsules.

11. The personal care article of claim 3 wherein said odor control agent includes an essential oil.

12. The personal care article of claim 3 wherein said odor control agent includes a zeolite.

13. The personal care article of claim 1 wherein said porous layer comprises a fabric.

14. The personal care article of claim 3 wherein said patch is releasably-attached to said first encasing layer.

15. The personal care article of claim 1 wherein said porous layer defines a pocket upon said first encasing layer.

16. The personal care article of claim 15 wherein said patch fits entirely within said pocket.

17. A personal care article comprising:
    first and second encasing layers, wherein said first encasing layer comprises a liquid permeable liner;
    an absorbent core positioned between said first and second encasing layers;
    a patch having a sealed containment area and comprising a first barrier layer attached to a second barrier layer and wherein at least a portion of said second barrier layer is detachable from said first barrier layer; and
    an odor control agent within said containment area of said patch wherein said odor control agent is discharged from said containment area upon detaching at least a portion of said second barrier layer; and
    an outermost porous layer directly attached to said first encasing layer, said outermost porous layer having a Frazier air permeability of at least about 10 m$^3$/m$^2$/minute and wherein said outermost porous layer extends over at least a portion of said first encasing layer and said patch and further wherein said patch is located between said outermost porous layer and said first encasing layer.

18. The personal care article of claim 17 wherein said second encasing layer comprises a liquid impermeable outer cover.

19. The personal care article of claim 17 wherein said second barrier layer is proximate said outermost porous layer.

20. The personal care article of claim 17 wherein said patch contains a carrier and said odor control agent is located within said carrier.

21. The personal care article of claim 17 wherein said patch is attached to said first encasing layer.

22. The personal care article of claim 17 further comprising an adhesive layer, said adhesive layer positioned between and attaching said first barrier layer of said patch and said first encasing layer.

23. The personal care article of claim 19 wherein said porous layer and said patch are positioned adjacent an end margin of said personal care article.

24. The personal care article of claim 23 wherein said porous layer comprises an elastic band material extending across substantially the entire length of said end margin.

25. The personal care article of claim 17 wherein said odor control agent is maintained within a polymer matrix.

26. The personal care article of claim 20 wherein said carrier comprises microcapsules and further wherein said second barrier layer of said patch is attached to said microcapsules.

27. The personal care article of claim 19 wherein said odor control agent includes an essential oil.

28. The personal care article of claim 19 wherein said odor control agent includes a zeolite.

29. The personal care article of claim 19 wherein said porous layer comprises a fabric.

30. The personal care article of claim 17 wherein said patch is releasably-attached to said first encasing layer.

31. The personal care article of claim 17 wherein said porous layer defines a pocket upon said first encasing layer.

32. The personal care article of claim 31 wherein said patch fits entirely within said pocket.

33. A personal care article comprising:
first and second encasing layers;
an absorbent core positioned between said first and second encasing layers;
a patch including an odor control agent, wherein said patch contains a carrier and said odor control agent is located within said carrier; and
an outermost porous layer directly attached to said first encasing layer, said outermost porous layer having a Frazier air permeability of at least 10 $m^3/m^2$/minute and wherein said outermost porous layer extends over at least a portion of said first encasing layer and said patch and further wherein said patch is located between said outermost porous layer and said first encasing layer;
wherein said patch comprises a first barrier layer and a second barrier layer and wherein said second barrier layer is proximate said outermost porous material and further wherein at least a portion of said second barrier layer is removable;
and further wherein said carrier comprises microcapsules and further wherein said second barrier layer of said patch is attached to said microcapsules.

34. A personal care article comprising:
first and second encasing layers;
an absorbent core positioned between said first and second encasing layers;
a patch including an odor control agent, wherein said patch is releasably-attached to said first encasing layer; and
an outermost porous layer directly attached to said first encasing layer, said outermost porous layer having a Frazier air permeability of at least 10 $m^3/m^2$/minute and wherein said outermost porous layer extends over at least a portion of said first encasing layer and said patch and further wherein said patch is located between said outermost porous layer and said first encasing layer;
wherein said patch includes a sealed cavity formed by at least one barrier layer and wherein said odor control agent is contained within said cavity.

35. A personal care article comprising:
first and second encasing layers;
an absorbent core positioned between said first and second encasing layers;
a patch including an odor control agent; and
an outermost porous layer directly attached to said first encasing layer, said outermost porous layer having a Frazier air permeability of at least 10 $m^3/m^2$/minute and wherein said outermost porous layer extends over at least a portion of said first encasing layer and defines a pocket upon said first encasing layer and said patch and further wherein said patch is located between said outermost porous layer and said first encasing layer.

36. The personal care article of claim 35 wherein said patch fits entirely within said pocket.

37. The personal care article of claim 1, wherein said first encasing layer comprises a topsheet.

38. The personal care article of claim 1, wherein said second encasing layer comprises a cover.

39. The personal care article of claim 1, wherein said outermost porous layer comprises a waistband.

40. The personal care article of claim 17, wherein said first encasing layer comprises a topsheet.

41. The personal care article of claim 17, wherein said second encasing layer comprises a cover.

42. The personal care article of claim 17, wherein said outermost porous layer comprises a waistband.

43. The personal care article of claim 33, wherein said first encasing layer comprises a topsheet.

44. The personal care article of claim 33, wherein said second encasing layer comprises a cover.

45. The personal care article of claim 33, wherein said outermost porous layer comprises a waistband.

46. The personal care article of claim 34, wherein said first encasing layer comprises a topsheet.

47. The personal care article of claim 34, wherein said second encasing layer comprises a cover.

48. The personal care article of claim 34, wherein said outermost porous layer comprises a waistband.

49. The personal care article of claim 35, wherein said first encasing layer comprises a topsheet.

50. The personal care article of claim 35, wherein said second encasing layer comprises a cover.

51. The personal care article of claim 35, wherein said outermost porous layer comprises a waistband.

* * * * *